United States Patent
Kato et al.

[11] Patent Number: 6,012,282
[45] Date of Patent: Jan. 11, 2000

[54] METHOD FOR CONTROLLING ENGINE EXHAUST GAS SYSTEM

[75] Inventors: Nobuhide Kato, Ama-gun; Hiroshi Kurachi, Nagoya, both of Japan

[73] Assignee: NGK Insulators, Ltd., Japan

[21] Appl. No.: 08/876,396

[22] Filed: Jun. 16, 1997

[30] Foreign Application Priority Data

Jun. 21, 1996 [JP] Japan ..................................... 8-161218
May 28, 1997 [JP] Japan ..................................... 9-139021

[51] Int. Cl.$^7$ ........................................................ F01N 3/00
[52] U.S. Cl. ................................ 60/274; 60/277; 60/276; 60/285; 123/688
[58] Field of Search ............................. 60/274, 277, 276, 60/285, 301; 73/23.32, 23.31, 31.06; 205/781; 204/424, 425, 426, 427, 428, 429; 123/688

[56] References Cited

U.S. PATENT DOCUMENTS

| | | | |
|---|---|---|---|
| 4,927,517 | 5/1990 | Mizutani et al. | 204/406 |
| 5,444,974 | 8/1995 | Beck et al. | 60/274 |
| 5,452,576 | 9/1995 | Hamburg et al. | 60/274 |
| 5,643,429 | 7/1997 | Wachsman | 205/781 |

FOREIGN PATENT DOCUMENTS

| | | | |
|---|---|---|---|
| 0 678 740 | 10/1995 | European Pat. Off. | 27/407 |
| 0 678 740 A1 | 10/1995 | European Pat. Off. . | |
| 4-65224 | 10/1992 | Japan . | |

*Primary Examiner*—Thomas Denion
*Assistant Examiner*—Binh Tran
*Attorney, Agent, or Firm*—Parkhurst & Wendel, L.L.P.

[57] ABSTRACT

A method for controlling an engine exhaust gas system includes the steps of detecting an air-fuel ratio of exhaust gas discharged from an internal engine by an oxygen sensor, controlling the exhaust gas to near the stoichiometric air-fuel ratio by a closed-loop control referring to a resultant signal, and leading the exhaust gas to a three-way catalyst to treat nitrogen oxide, hydrocarbon and carbon monoxide. A nitrogen oxide sensor is provided downstream of the three-way catalyst, and a control value of air-fuel ratio by a closed loop control by the oxygen sensor is corrected to set the nitrogen oxide concentration to a predetermined value in accordance with an output of the nitrogen oxide sensor. The deterioration of the three-way catalyst and/or oxygen sensor is detected by comparing a change in control corrected value for the air-fuel ratio of closed loop control referring to an output of the nitrogen oxide sensor with a predetermined value.

13 Claims, 7 Drawing Sheets

METHOD FOR CONTROLLING ENGINE EXHAUST GAS SYSTEM

BACKGROUND OF THE INVENTION AND RELATED ART STATEMENT

The present invention relates to a method for controlling an engine exhaust gas system using an oxygen sensor, a three-way catalyst and a nitrogen oxide sensor and more specifically to a method for controlling an engine exhaust gas system, which can accurately control the exhaust amount of nitrogen oxide (hereinafter, referred to as NOx) and further detect the deterioration of a three-way catalyst easily.

There has conventionally been employed a method for controlling an air fuel ratio and removing harmful matters such as NOx, carbon monoxide and hydrocarbon in exhaust gas of the internal engine of an automobile by using an oxygen sensor and a three-way catalyst. On account of dispersion in characteristics of the oxygen sensor and change with time in characteristics of the sensor itself, however, the control point varied, so that the size of a three-way catalyst and the amount of noble metal carried thereon needed securing to a little excess to restrict the discharge of harmful matters within a determined value. Alternatively, there has been a method for correcting dispersion in control point by placing an oxygen sensor also downstream of a catalyst.

Even according to any of these methods, however, there were drawbacks in that the air fuel ratio deviates from a setup value, a great amount of NOx, carbon monoxide (CO), hydrocarbon (HC) or the like is exhausted suddenly and the regulating value for exhaust gas is apt to be exceeded under transient operating conditions such as acceleration or deceleration. As for methods for detecting the deterioration of a catalyst, there have been proposed a method for detecting the deterioration as a change in the oxygen adsorption capacity of a catalyst in accordance with the amplitude or response time of output of an oxygen sensor by using the oxygen sensor disposed downstream of the catalyst, and a method for detecting the amount of unreacted components in accordance with an increase in temperature accompanying combustion by using a temperature sensor with the catalyst. However, these methods served to only indirectly detect the deterioration of a catalyst and accordingly had a low accuracy.

Furthermore, there is known a nitrogen oxide sensor described in European Patent Publication 0678740A1. This sensor was slower in response speed than a conventional concentration cell oxygen sensor and it was difficult to directly control the air fuel ratio of a three-way catalyst system by only this sensor.

Besides, Japanese Patent Publication No. 4-65224 discloses a system for controlling an air fuel ratio by using an oxygen sensor installed in front of a catalyst. This system monitors the NOx and CO concentrations at the same time by using a NOx sensor and a CO sensor. A resistance value of the NOx sensor changes in accordance with NOx concentrations by using semiconductor, e.g., $SnO_2$, and a resistance value of the CO sensor changes in accordance with CO concentrations by using $SnO_2$ in the same manner. Both the NOx sensor and the CO sensor are provided downstream of the catalyst. The air fuel ratio is corrected to a rich direction if the NOx concentration is greater than a predetermined value because NOx concentration increases when the oxygen sensor deteriorated to a lean side. The air fuel ratio is corrected to a lean direction if the CO concentration is greater than a predetermined value because CO or HC concentration increases when the oxygen sensor deteriorated to a rich side. Accordingly, the NOx, CO or HC concentration can be minimized even if the oxygen sensor deteriorates.

In this system, however, the air fuel ratio control is not subjected to correction if the NOx, CO and HC concentration is equal to or less than a predetermined value in order to control an increase in harmful gas component due to the deterioration of an oxygen sensor, the control point for air fuel ratio varied to a great extent in the window of a three-way catalyst though the harmful gas component is below a regulating value. Additionally, there was a drawback that a sensor for measuring NOx, component on the lean side and another sensor for measuring CO or HC, component on the rich side are required (in addition to an oxygen sensors, two gas sensor are required) because it is not obvious whether an oxygen sensor deteriorates to the rich side or to the lean side. Thus, this system had critical problems such as the need for two gas sensors and correction control function for two sensors, dispersion in harmful components, and excessive cost.

In addition, this system has another drawback that the deterioration of a catalyst cannot be detected.

SUMMARY OF THE INVENTION

To solve the above-mentioned drawbacks of the background art, the present invention provides a method for controlling an engine exhaust gas system, capable of minimizing dispersion in the exhaust of harmful components with a simple system, restricting a sudden exhaust of CO or HC even under transient operating conditions, downsizing and cost-saving of a three-way catalyst and further accurately detecting a deterioration of a three-way catalyst.

According to the present invention, there is provided a method for controlling an engine exhaust gas system, comprising the steps of: detecting an air-fuel ratio of exhaust gas discharged from an internal engine by an oxygen sensor; controlling the exhaust gas to near the stoichiometric air-fuel ratio by a closed-loop control referring to a resultant signal; and leading the exhaust gas to a three-way catalyst to treat nitrogen oxide, hydrocarbon and carbon monoxide, wherein a nitrogen oxide sensor is provided downstream of the three-way catalyst and a control value of air-fuel ratio by a closed loop control by the oxygen sensor is corrected to set the nitrogen oxide concentration to a predetermined value in accordance with an output of the nitrogen oxide sensor.

Further, according to the present invention, there is provided a method for controlling an engine exhaust system comprising the steps of: detecting an air-fuel ratio of exhaust gas discharged from an internal engine by an oxygen sensor; controlling the exhaust gas to near the stoichiometric air-fuel ratio by a closed loop control referring to a resultant signal; and leading the exhaust gas to a three-way catalyst to treat nitrogen oxide, hydrocarbon and carbon monoxide, wherein a nitrogen oxide sensor is provided downstream of the three-way catalyst; and the nitrogen oxide concentration is set to a predetermined value by correcting a control value for air-fuel ratio by a closed loop control by the oxygen sensor in accordance with an output of the nitrogen oxide sensor, and the deterioration of the three-way catalyst and/or the oxygen sensor is detected, in accordance with the extent of correction for the control value of an air-fuel ratio or the change width thereof.

Incidentally, it is preferable that the nitrogen oxide sensor comprises main pump means including an electrochemical pump cell comprising a substrate composed of oxygen ion conductive solid electrolyte, an inside pump electrode and an outside pump electrode formed on the inner surface and outer surface of the substrate, respectively, and the main pump means treating oxygen contained in the measuring gas introduced from an external space by pumping processing on the basis of a control voltage applied between the inside pump electrode and the outside pump electrode, and electric signal conversion means for generating an electric signal corresponding to the quantity of oxygen generated by decomposition or reduction of NOx contained in the measuring gas after being treated by the pumping processing by the main pump means in which one side thereof has a pair of detection electrodes formed on the side where the measuring gas that was treated by pumping processing by the main pump means is introduced.

Specifically, a nitrogen oxide sensor having the following constituents is desirable:

(a) First internal space communicated to an external measuring gas existing space;

(b) First diffusion controlled means for leading the measuring gas containing a measuring component from the measuring gas existing space to the first internal space under a predetermined diffusion resistance;

(c) First oxygen pump means for performing oxygen pumping of the first internal space by electrifying between a pair of electrodes by using a first electrochemical cell comprising a first oxygen ion conductive solid electrolyte and a pair of electrodes provided in contact therewith, and controlling the oxygen partial pressure in the atmosphere in the first internal space to a predetermined low value that does not allow NO substantially to be decomposed;

(d) Second internal space communicated to the first internal space;

(e) Second diffusion controlled means for leading the controlled atmosphere in the first internal space to the second internal space under a second diffusion resistance;

(f) NOx decomposing catalyst disposed in the second internal space;

(g) Second oxygen pumping means for pumping out oxygen generated mainly by decomposition of NOx by electrifying between a pair of electrodes by using a second electrochemical cell comprising a second oxygen ion conductive solid electrode and a pair of electrodes provided in contact therewith, or pumping out the oxygen produced by the reduction of NOx due to a strongly reductive atmosphere created on the surface of an electrode exposed into the second internal space by electrifying the electrode by a second electrochemical cell of the one electrode exposed and another electrode; and (h) Current detection means for detecting a pumping current flowing by the pumping operation of the second electrochemical cell.

Incidentally, the above (g) and (h) may be substituted by the following (g) and (h) so as to constitute the aforementioned nitrogen oxide sensor.

(g) Oxygen concentration detection means generating an electromotive force according to a partial pressure of oxygen generated mainly by decomposition of NOx, which derives from a difference in an oxygen partial pressure between surfaces of a pair of electrodes, by using a second electrochemical cell comprising a second oxygen ion conductive solid electrolyte and a pair of electrodes being in contact with the second oxygen ion conductive solid electrolyte.

(h) Voltage detection means for detecting an electromotive force generated in the oxygen concentration detection means.

Or, a nitrogen oxide sensor having the following constituents is desirable:

(a) Internal space communicated to an external measuring gas existing space;

(b) Diffusion controlled means for leading the measuring gas containing a measuring gas component from the external measuring gas existing space to the internal space under a predetermined diffusion resistance;

(c) Oxygen pumping means for performing oxygen pumping of the first internal space by electryfying between a pair of electrodes by using a first electrochemical cell comprising a first oxygen ion conductive solid electrolyte and a pair of electrodes provided in contact therewith to control the oxygen partial pressure in the atmosphere of the internal space to a predetermined low value that is substantially incapable of decomposing NO;

(d) An oxide semiconductor whose resistance changes by nitrogen oxide disposed in the internal space; and (e) resistance detection means for measuring a resistance value of the oxide semiconductor.

That is, in the present invention, the function of purifying harmful components by lean and rich alternating operations near the stoichiometric air-fuel ratio by means of a conventional oxygen sensor and three-way catalyst is utilized as it is to detect the amount of NOx contained in exhaust gas after passing through the three-way catalyst, the control point of air-fuel ratio is finely adjusted by the feedback of the output thereof, and thus a value of NOx is made a predetermined value.

Besides, a method of the present invention detects the degree of deterioration in three-way catalyst and/or oxide sensor in accordance with the extent of the above fine adjustment. Further, the method measures a value of the pumping current needed for removing the obstructing components, which are oxygen gas and combustible gases such as HC, in measuring NOx with a nitrogen oxide sensor so as to obtain a predetermined oxygen partial pressure, i.e., the residual oxygen concentration after the reaction of oxygen with combustible components such as HC in exhaust gas, thereby detecting the degree of deterioration of a three-way catalyst and/or an oxygen sensor.

PREFERRED EMBODIMENTS OF THE INVENTION

Hereinafter, a method for controlling an engine exhaust gas system according to the present invention is described A specific example of a method for correcting a control point for air fuel ratio in accordance with an output of an NOx sensor and its advantages will be described in detail.

Figure 1:
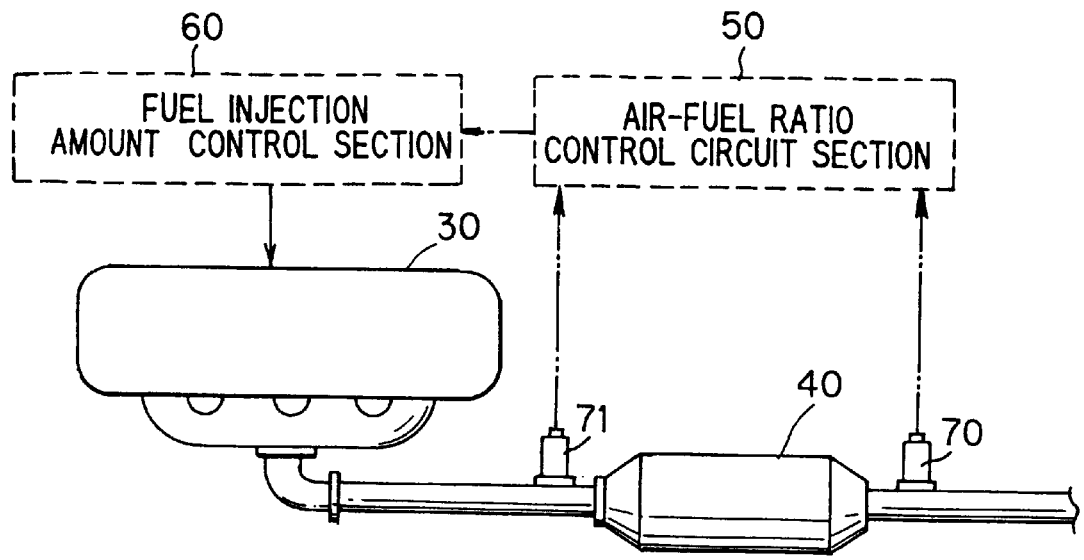
FIG. 1 is an explanatory view of one embodiment of a method for controlling an engine exhaust gas system according to the present invention.
Figure 2:
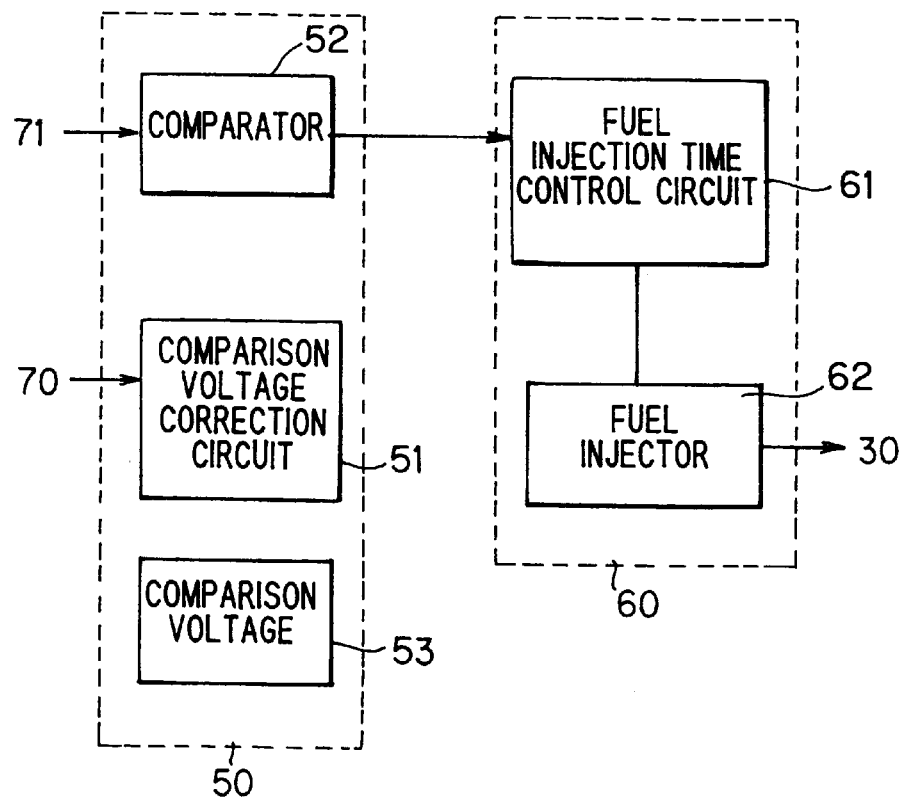
FIG. 2 is a block illustration of an air-fuel ratio control circuit section of FIG. 1.
Figure 3:
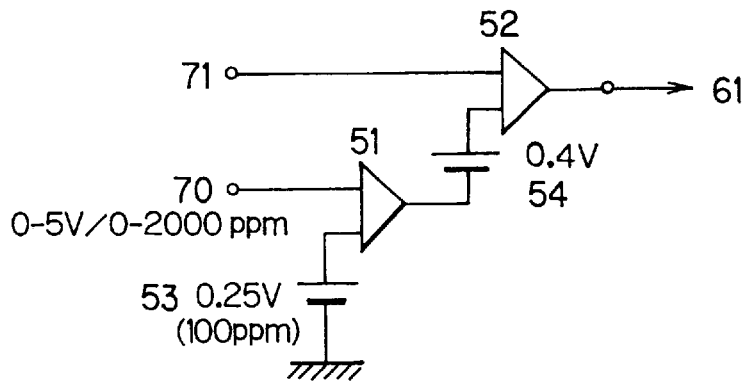
FIG. 3 is a circuit illustration of an air-fuel ratio control circuit section of FIG. 1.

FIG. 1 is an explanatory view showing an embodiment of a method for controlling an engine exhaust gas system according to the present invention. FIG. 2 is a block illustrative diagram showing an air-fuel ratio control circuit section of FIG. 1. and FIG. 3 is a circuit illustration of an air-fuel ratio control circuit section of FIG. 1.

In FIG. 1, a three-way catalyst 40 is provided at the exhaust gas system of an engine 30, while an oxygen sensor 1 and a nitrogen oxide sensor 70 are provided upstream and downstream of the three-way catalyst 40, respectively. In this engine exhaust gas system, the air-fuel ratio of exhaust gas exhausted from the engine 30 is detected with the oxygen sensor 71 and is controlled near the stoichiometric air-fuel ratio with a closed loop control using the resultant signal. This exhaust gas is led to the three-way catalyst 40, from which harmful components such as nitrogen oxide (NOx), hydrocarbon (HC) and carbon monoxide (CO) are removed.

Here, as oxygen sensor 71, a sensor comprising an oxygen concentration cell using a zirconia porcelain as solid electrolyte, an all range type sensor for determining a diffusion limiting current by an oxygen pump, a sensor according to a change in the resistance of an oxide semiconductor such as titania, or the like is available. As NOx sensor 70, a sensor with an oxygen pump using the zirconia porcelain, e.g., described in European Patent Publication 0678740A1, as solid electrode, a sensor which measures a change in electromotive force being generated in an electrochemical cell with controlling an oxygen concentration by combining an oxygen pump and an electrochemical cell, a sensor according to a change in the resistance of an oxide semiconductor, a sensor for measuring a change in the resistance of an oxide semiconductor under control of oxygen concentration, comprising a combination of an oxygen pump and an oxide semiconductor, or the like is available.

With respect to an air-fuel ratio control circuit section 50 and a control section 60 for fuel injection amount, one example thereof will be described referring to FIGS. 2 and 3.

As shown in FIGS. 2 and 3, a 0–5 V output signal of the NOx sensor (a sensor signal is so processed as to issue an output of 0–5 V for an NOx concentration of 0–2000 ppm) is compared with a comparison voltage (0.25 V) 53 corresponding to 100 ppm and superposed to the comparison voltage (0.4 V) of a comparator (comparative amplifier) 52 in an oxygen sensor 71 by means of a comparison amplifier 51 comprising a comparison voltage correction circuit. Thereby, the comparison voltage substantially ascends if the NOx concentration is greater than 100 ppm, an output in a lean condition of air-fuel ratio is issued from the air-fuel ratio control circuit section 50 and transferred to the fuel jet time control circuit 61 of a control section 60 for fuel injection amount, so that the control point for air fuel ratio moves in the increasing direction of fuel injected from a fuel injector 62 to an engine 30, e.g., in a decreasing direction of NOx.

By the adoption of this correction control, the NOx concentration is always controlled near 100 ppm, thereby eliminating a mass generation of NOx during the acceleration under FTP (Federal Test Procedure) running condition and reducing dispersion in the exhaust amount of NOx, HC and CO due to dispersion in the characteristic of an oxygen sensor.

Figure 4:
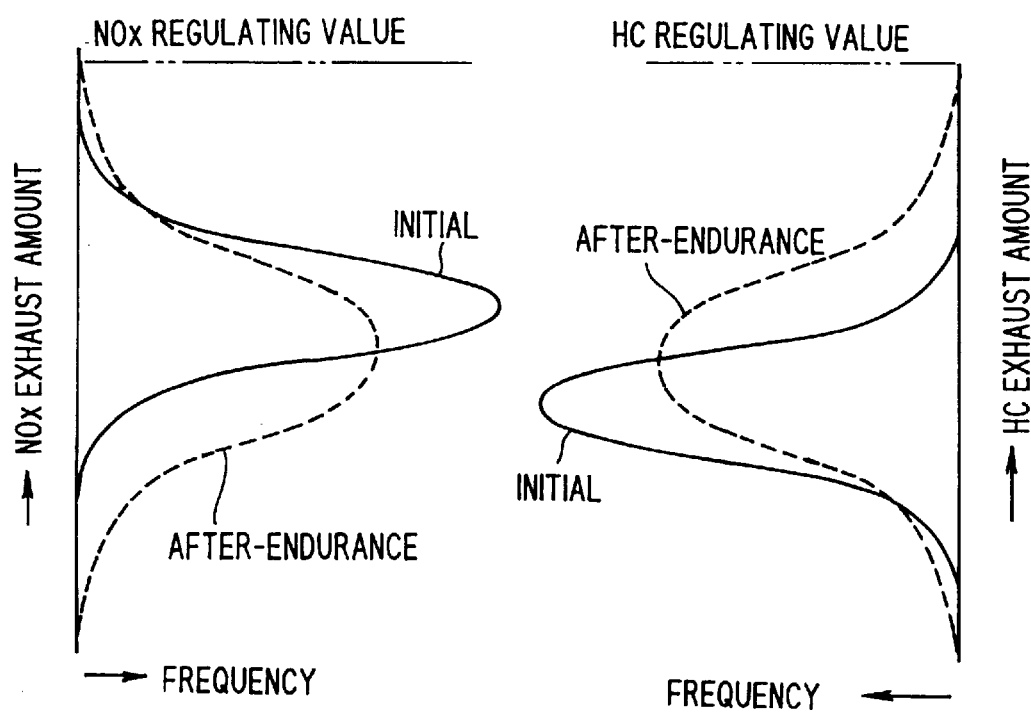
FIG. 4 is a graph showing the exhaust amount of NOx and hydrocarbon in exhaust gas after passing through a three-way catalyst in a case of using an air-fuel ratio control by means of a conventional oxygen sensor alone.
Figure 5:
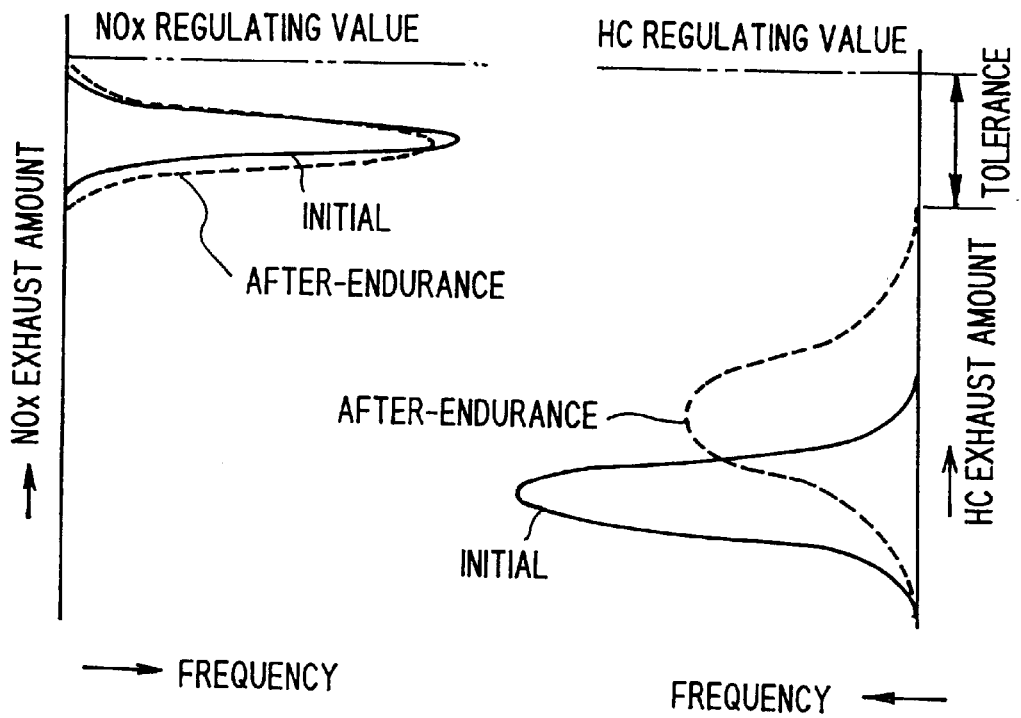
FIG. 5 is a graph showing the exhaust amount of NOx and hydrocarbon in exhaust gas after passing through a three-way catalyst in a case of performing a correction by referring to an NOx sensor according to the present invention.

FIGS. 4 and 5 are graphs of the exhaust amount of NOx and hydrocarbon in exhaust gas after passing through a three-way catalyst for a case of using an air-fuel ratio control by a conventional oxygen sensor alone and for a case of performing a correction by an NOx sensor according to the present invention, respectively.

In the case of using the air-fuel ratio control by a conventional oxygen sensor alone, as shown in FIG. 4, dispersion in the characteristic of an oxygen sensor and dispersion in the purification characteristic of a catalyst leads to a large dispersion in the exhaust amount of NOx and hydrocarbon and further this dispersion increases due to a change with time during use. To satisfy the exhaust gas regulating value under conditions of large dispersion, using a large-sized catalyst or a great carrying amount of noble metal catalyst was necessary.

In contrast, in a case where a correction by an NOx sensor according to the present invention is performed, since the concentration of exhausted NOx can be controlled independently of the characteristic of an oxygen sensor and the purification characteristic of a catalyst as shown in FIG. 5, the exhaust amount of NOx can be accurately controlled to a predetermined value. Thus, it is only necessary to set the catalyst to a necessary minimum size, and further because the control point for air-fuel ratio becomes accurate, the exhaust amounts of HC and CO are also reduced.

Figure 6:
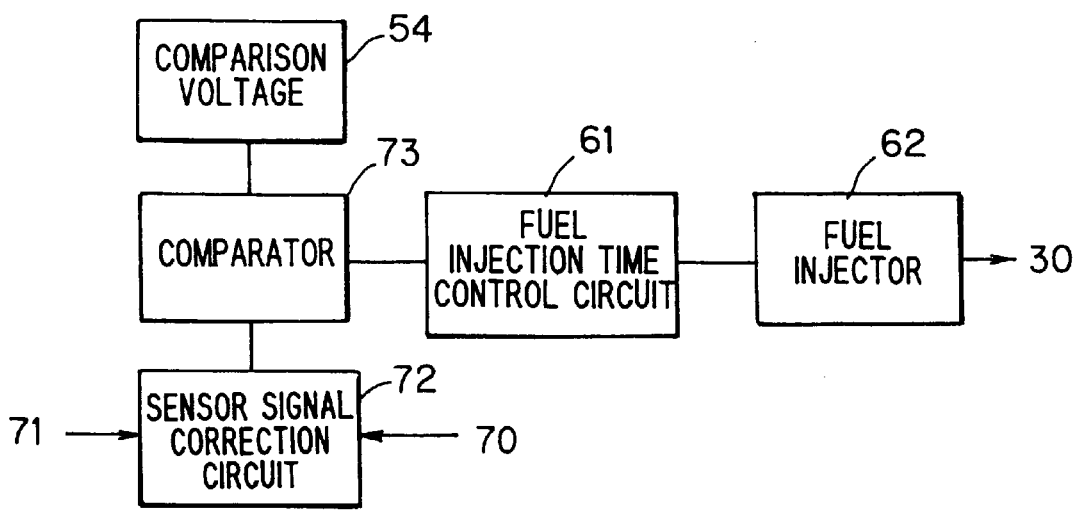
FIG. 6 is a block diagram of one example of superimposing an output of an NOx sensor on an output of an oxygen sensor.

Alternatively, as a correction method for air fuel-ratio in accordance with an output of an NOx sensor, an output of the NOx sensor 70 is superposed on an output of the oxygen sensor 71 by inverting a polarity in a sensor signal correction circuit 72 and this correction signal may be compared with a comparison voltage (0.4 V) 54 in a comparator 73 as shown in FIG. 6. Thereby, when the NOx concentration is more than 100 ppm, the output of the oxygen sensor substantially lowers and an output in a lean condition of air fuel-ratio is transferred to a control circuit 61 for fuel injection time, so that the control point for air fuel ratio moves in the increasing direction of fuel injected from a fuel injector 62 into an engine 30, i.e., in the decreasing direction of NOx.

Figure 7:
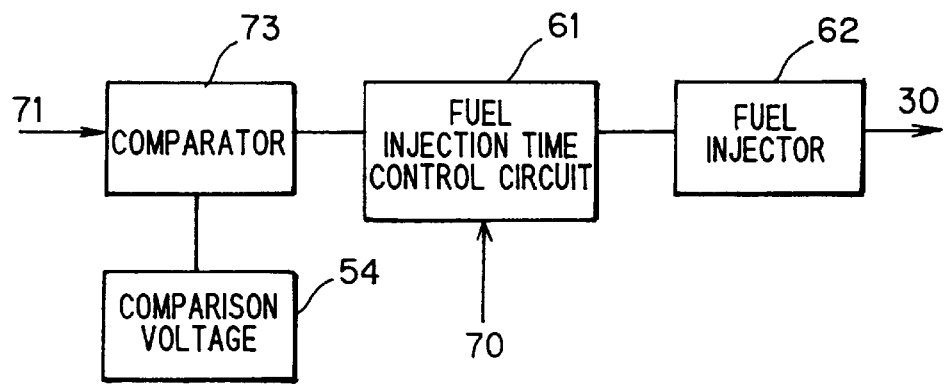
FIG. 7 is a block diagram of one example of adding an output of an NOx sensor to a fuel injection time control circuit.
Figure 8:
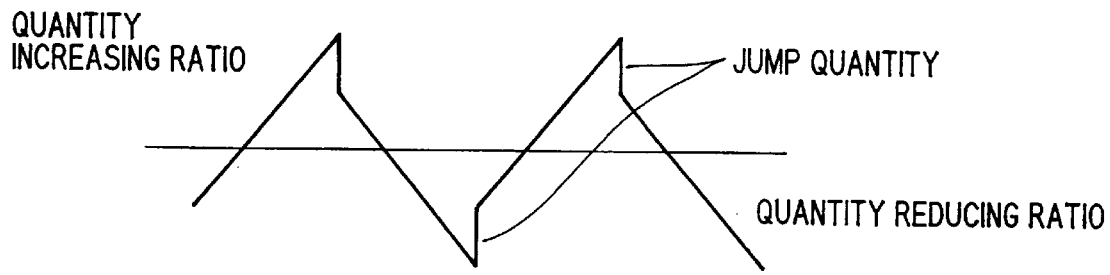
FIG. 8 is a chart showing a control signal for fuel injection amount.

Furthermore, as shown in FIG. 7, there may be alternatively employed a method comprising the steps of comparing an output of the oxygen sensor 71 with the comparison voltage (0.4 V) 54 by a comparator 73, transferring the resultant signal to a fuel injection time control circuit 61 and moreover adding an output of an NOx sensor 70 to a control circuit 61 for fuel injection time to adjust the quantity increasing ratio, the quantity decreasing ratio, the jump amount, etc., of a control signal for fuel injection quantity shown in FIG. 8.

Incidentally, it is preferable in view of gas regulation measures to replace the NOx concentration information from an NOx sensor, gas flow rate information, and running speed information with NOx exhaust quantity (g/mile) information and correct the air-fuel ratio.

Next, one embodiment of a method for detecting the deterioration of a three-way catalyst and/or oxide sensor by referring to the extent of correction of the control point for air-fuel ratio of an oxygen sensor in accordance with an output of an NOx sensor according to the present invention and its advantages will be described.

Figure 9:
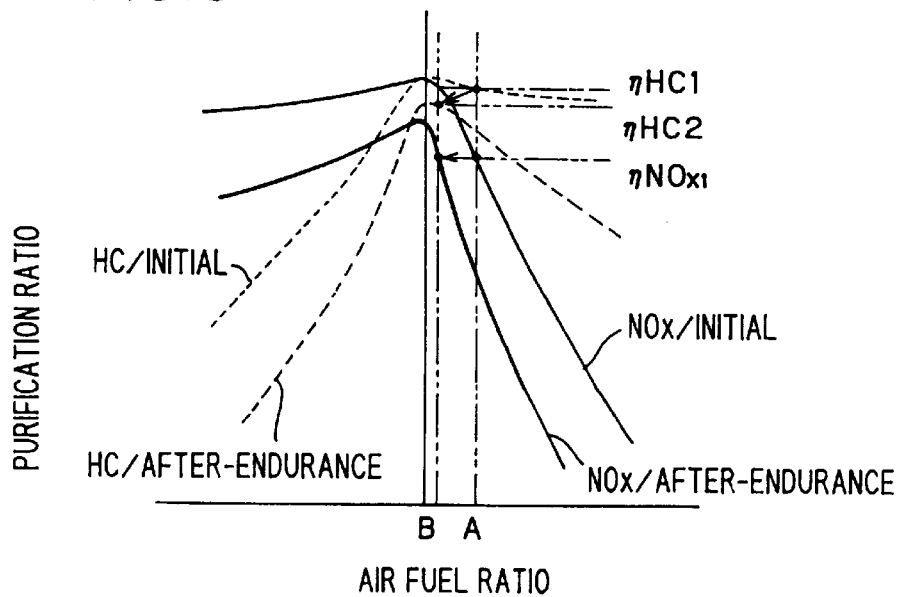
FIG. 9 is a graph showing the initial and after-endurance purification rate characteristic of a three-way catalyst.

FIG. 9 is a graph showing the initial and after-endurance purification rate characteristics of a three-way catalyst. ηNOx1 is a purification required to set the NOx concentration to 100 ppm under a predetermined running condition. When a three-way catalyst deteriorates with time, the purification rates of NOx and HC lower together. To maintain the NOx concentration at 100 ppm even after a long running period, the control point for air-fuel ratio moves from the point A to the point B and as a result, the purification rate of HC lowers from ηHC1 to ηHC2. Thus, the difference of correction signals A–B can be employed as a measure for representing the degree of deterioration of a three-way catalyst and for example, a change in the extent of correction signals and the exhaust amount of HC have correlation under running condition of a predetermined constant speed. The exhaust amount of HC is calculated from this correlation and the judgment of deterioration can be performed.

Figure 10:
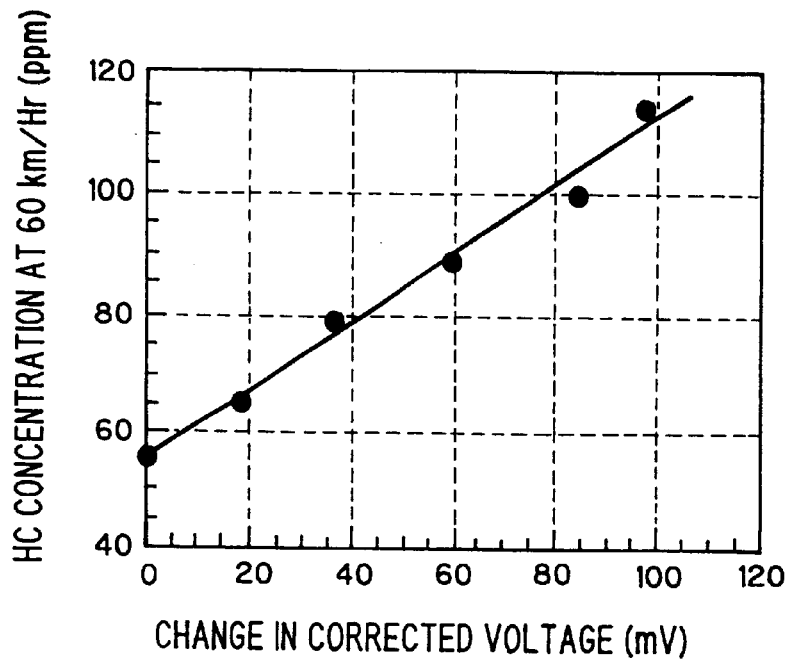
FIG. 10 is a graph showing the correlation between the corrected voltage and the HC concentration under running conditions of constant speed, evaluated using a new three-way catalyst and five endurance level three-way catalysts.
Figure 11:
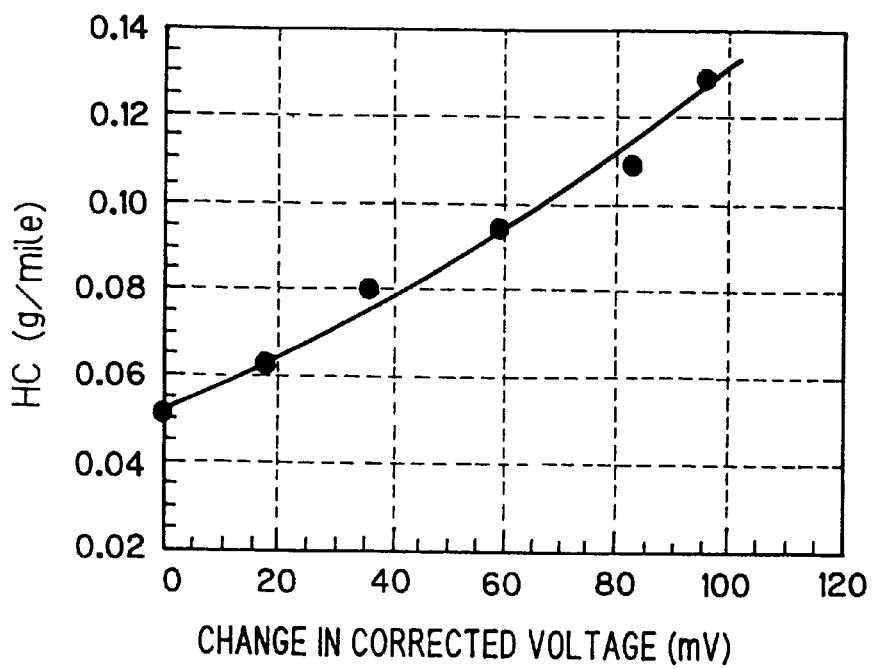
FIG. 11 is a graph showing the correlation between the corrected voltage and the HC exhaust amount in the FTP running mode, evaluated using a new three-way catalyst and five endurance level three-way catalysts.

FIGS. 10 and 11 show the relations of a change in correction voltage with the HC concentration under running condition of constant speed and the HC exhaust amount in the FTP running mode measured using a new three-way catalyst and 5 endurance levels of three-way catalysts, both of which are found to have a good correlation.

Next, a specific example of method for detecting the deterioration of a three-way catalyst and/or oxygen sensor by referring to a pumping current of the first electrochemical pump cell in an NOx sensor and its advantages will be described.

Figure 12:
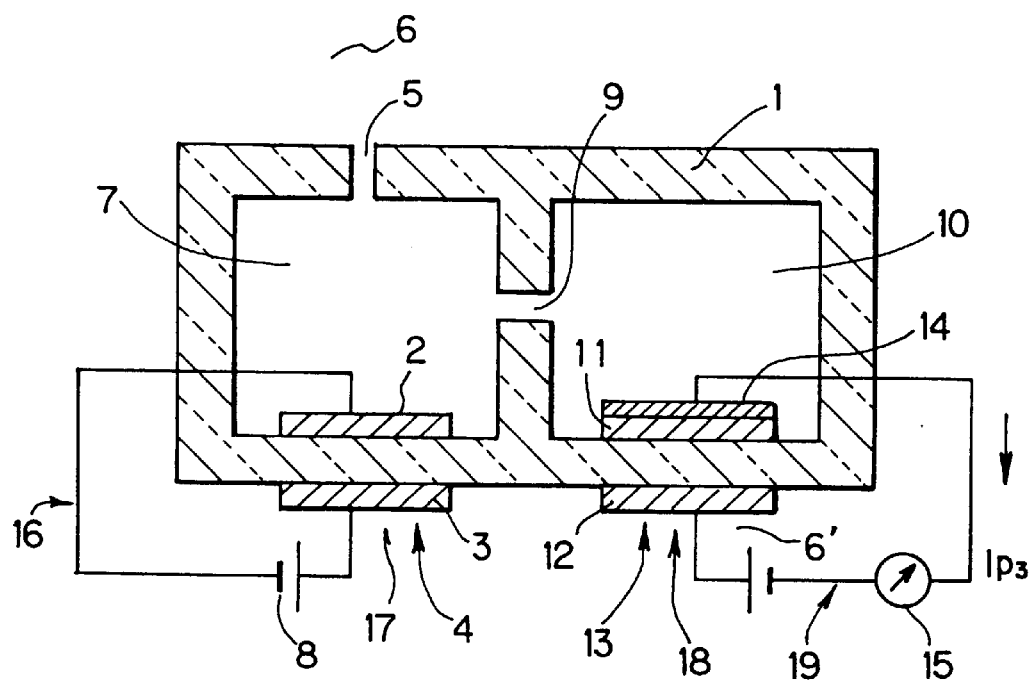
FIG. 12 is an explanatory view of the basic configuration of an NOx sensor according to the present invention.

An NOx sensor of a scheme a showing the basic configuration in FIG. 12 may be used. In FIG. 12, a first electrochemical pump cell 4 is constituted of a partition wall 1, an inside pump electrode 2, and an outside pump electrode 3 such as platinum. The electrodes 2 and 3 are provided on both surfaces of a partition wall 1 made of oxygen ion conductive solid electrolyte such as zirconia porcelain.

Between the inside pump electrode 2 and the outside pump electrode 3 of the first electrochemical pump cell 4, an electric circuit 16 is provided, which main pumping means 17 is so arranged as to apply a control voltage from a power source 8 thereto. In this configuration, the measuring gas is introduced from the measuring gas space 6 into a first internal space 7 via a first diffusion controlled passage 5. By a control voltage applied to between the inside pump electrode 2 and the outside pump electrode 3 from the power source 8, the oxygen partial pressure in the first internal space 7 is controlled to a predetermined, preferable low value that does not allow NO to be reduced.

The atmosphere in an internal space 7 with this oxygen partial pressure is introduced into a second internal space 10 via a second diffusion controlled passage 9. In the second internal space 10, an electric circuit 19 is provided between a detection electrode 11 and a reference electrode 12 disposed on both surfaces of the partition wall 1, all of which constitute electric signal conversion means 18. And, on the detection electrode 11, a catalyst 14 for accelerating the decomposition of NOx is provided.

Then, NOx in the atmosphere introduced into the second internal space 10 via the second diffusion controlled passage 9 is decomposed either by a catalyst 14 or under a low partial oxygen pressure, and at that time the generated oxygen is pumped out from the second internal space 10 to the reference gas existing space 6' by using a second electrochemical pump cell 13 under gas diffusion controlled conditions, and the NOx amount in the measuring gas is measured by referring to a value of current flowing through the second electrochemical pump cell 13. Incidentally, the second electrochemical pump cell 13 has only to detect the NOx concentration, and instead detectors of other schemes, e.g., oxide semiconductor whose resistance changes with different NOx concentrations.

As already described, the move amount of a control point for air-fuel ratio obtained when the NOx concentration after passing through a three-way catalyst is controlled to a predetermined value represents the degree of deterioration of the catalyst or an oxygen sensor. Accordingly, when this move amount reaches a predetermined value during monitoring, it can be judged that the catalyst has deteriorated.

With an NOx sensor of the scheme of FIG. 12, the value of the first electrochemical pump cell current (first pump current value) is a value corresponding to the residual oxygen concentration after oxygen in the measuring gas has reacted with combustible gases such as HC. If this value deviates from a predetermined range, a value of HC in the exhaust gas after gas passing through a three-way catalyst never fails to exceed a predetermined range. That is, for an initial three-way catalyst, the air-fuel ratio is controlled at the point A (to the lean side from the stoichiometric air-fuel ratio point) as shown in FIG. 9 and the oxygen concentration in exhaust gas is high, and the amount of combustible gases such as HC is small. Consequently, first pump current representing the residual oxygen concentration after the reaction of oxygen with combustible gases such as HC becomes a large value. When the control point moves in the rich direction as a result of deterioration with time of a three-way catalyst (point B of FIG. 9), the oxygen concentration in exhaust gas lowers, whereas the amount of combustible gases such as HC increases. Because of corresponding to the residual oxygen concentration after the reaction of oxygen with combustible gases such as HC, first pump current greatly lowers on account of the additive effect of a change in oxygen and a change in combustible gases such as HC.

Figure 13:
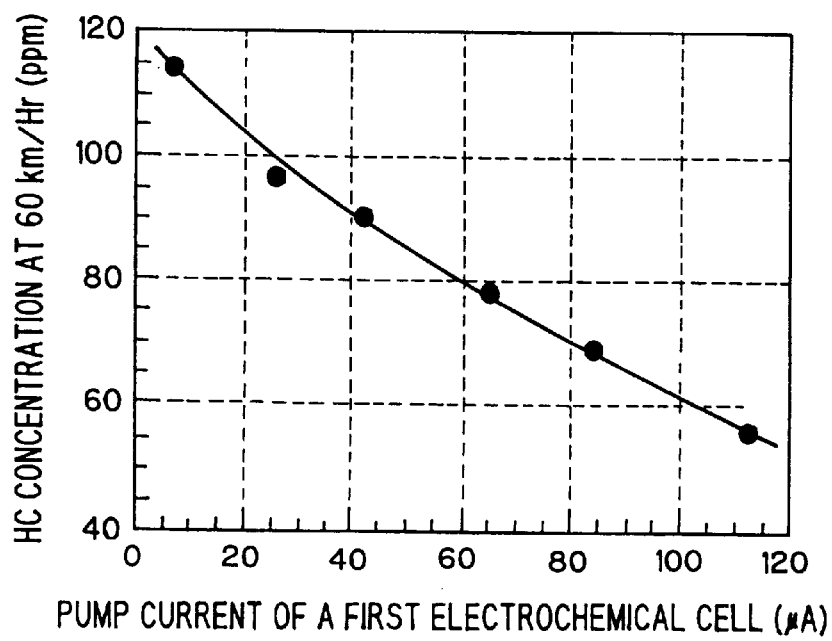
FIG. 13 is a graph showing the correlation between a value of pump current in a first electrochemical cell and the HC concentration under running conditions of constant speed, evaluated using a new three-way catalyst and five endurance level three-way catalysts.
Figure 14:
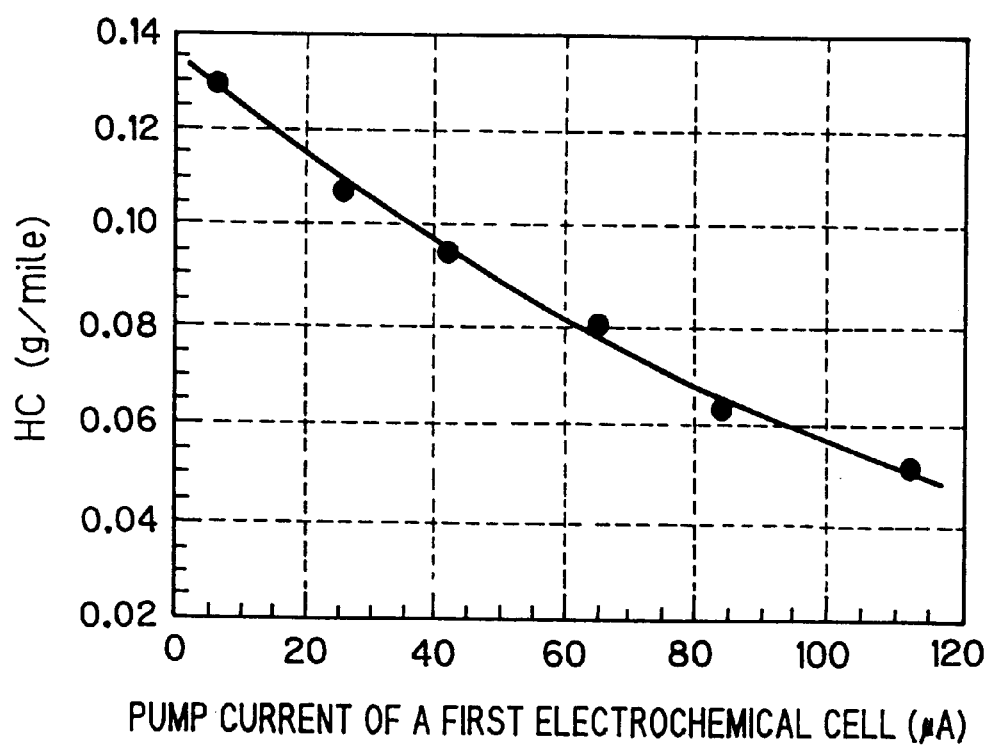
FIG. 14 is a graph showing the correlation between a value of pump current in a first electrochemical cell and the HC exhaust amount in the FTP running mode, evaluated using a new three-way catalyst and five endurance level three-way catalysts.

Incidentally, a value of current for the judgment of deterioration may be represented in terms of absolute value or width of changes. FIGS. 13 and 14 show the correlation of a value of pump current for a first electrochemical cell, i.e., the excessive oxygen amount with the HC concentration under running condition of constant speed and the HC exhaust amount in the FTP running mode measured using a new three-way catalyst and 5 endurance levels of three-way catalysts, both of which are found to have a good correlation.

(EXAMPLE)

On an automobile with a 1-liter volume three-way catalyst attached to a 2-liter displacement and 4 cylinder gasoline engine, 5 different oxygen sensors A–E in characteristic and an NOx sensor of FIG. 12 were mounted as shown in FIG. 1, the air-fuel ratio was corrected in the circuits of FIGS. 2 and 3 and the amounts of NOx and HC contained in exhaust gas were measured under conditions of the FTP driving mode.

According to the results shown in Table 1, even when oxygen sensors vary in characteristic, both NOx and HC in all five types of oxygen sensors satisfy the LEV (Low Emission Vehicle) standard values for US California automobile exhaust gas regulation, NOx$\leq$0. 20 g/mile and HC$\leq$0. 075 g/mile, if correction for the air-fuel ratio according to a NOx sensor was made. In contrast, the sensor D and E did not satisfy the standard values if no correction made.

Furthermore, in this automobile, oxygen sensors, a three-way catalyst and an NOx sensor were subjected to 50 kmile durability tests at the same time. As shown in Table 2, the results obtained revealed that all oxygen sensors satisfied the LEV after-endurance standard values, that NOx $\leq$0.20 g/mile and HC$\leq$0.075 g/mile, even if the characteristic of oxygen sensors or a catalyst deteriorates. In contrast, any one of the oxygen sensors did not satisfy the standard values if no correction made.

TABLE 1

| Oxygen sensor | With correction control | | Without correction control | |
| --- | --- | --- | --- | --- |
| | NO x (g/mile) | HC (g/mile) | NO x (g/mile) | HC (g/mile) |
| A | 0.16 | 0.04 | 0.18 | 0.04 |
| B | 0.17 | 0.04 | 0.15 | 0.05 |
| C | 0.16 | 0.05 | 0.13 | 0.06 |
| D | 0.16 | 0.05 | 0.10 | 0.08 |
| E | 0.17 | 0.04 | 0.08 | 0.12 |

TABLE 2

| Oxygen sensor | With correction control | | Without correction control | |
| --- | --- | --- | --- | --- |
| | NO x (g/mile) | HC (g/mile) | NO x (g/mile) | HC (g/mile) |
| A | 0.18 | 0.06 | 0.23 | 0.04 |
| B | 0.17 | 0.07 | 0.21 | 0.06 |
| C | 0.18 | 0.05 | 0.17 | 0.08 |
| D | 0.16 | 0.06 | 0.13 | 0.09 |
| E | 0.17 | 0.05 | 0.11 | 0.10 |

As obvious from the above description, according to a method for controlling an engine exhaust gas system of the present invention, the harmful components in engine exhaust gas can be controlled to a low concentration for a long period of time and the deterioration of a three-way catalyst and oxygen sensors in an exhaust gas purification system can be surely detected, which is industrially very useful.

What is claimed is:

1. A method for controlling an engine exhaust gas system, comprising the steps of:

detecting an air-fuel ratio of exhaust gas discharged from an internal engine by an oxygen sensor;

controlling said exhaust gas to near the stoichiometric air-fuel ratio by a closed-loop control referring to a resultant signal; and leading said exhaust gas to a three-way catalyst to treat nitrogen oxide, hydrocarbon and carbon monoxide;

measuring a nitrogen oxide concentration by a nitrogen oxide sensor provided downstream of said three-way catalyst;

providing a comparison signal based on the result obtained by comparing the measured nitrogen oxide concentration with a predetermined value of nitrogen oxide; and correcting the air-fuel ratio by a closed loop control based on said comparison signal so as to keep the nitrogen oxide concentration at said predetermined value.

2. The method for controlling engine exhaust gas systems as set forth in claim 1, wherein said nitrogen oxide sensor comprises main pump means including an electrochemical pump cell comprising a substrate composed of oxygen ion conductive solid electrolyte, an inside pump electrode and an outside pump electrode formed on the inner surface and outer surface of the substrate, respectively, and the main pump means treating oxygen contained in the measuring gas introduced from an external space by pumping processing on the basis of a control voltage applied between the inside pump electrode and the outside pump electrode, and electric signal conversion means for generating an electric signal corresponding to the quantity of oxygen generated by decomposition or reduction of NOx contained in the measuring gas after treated by the pumping processing by the main pump means in which one side thereof has a pair of detection electrodes formed on the side where the measuring gas that was treated by pumping processing by the main pump means is introduced.

3. The method for controlling engine exhaust gas systems as set forth in claim 2, wherein the deterioration of at least one of a three-way catalyst and oxygen sensor is detected by comparing a change in control corrected value for the air-fuel ratio of closed loop control referring to an output of said nitrogen oxide sensor with a predetermined value.

4. The method for controlling engine exhaust gas systems as set forth in claim 2, wherein the deterioration of at least one of a three-way catalyst and oxygen sensor is detected in accordance with a value of pump current required for the pumping of oxygen in the electrochemical pump cell of said nitrogen oxide sensor.

5. The method of controlling engine exhaust gas systems as set forth in claim 2, wherein the deterioration of at least one of a three-way catalyst and an oxygen sensor or both is detected in accordance with a change of at least one of pump current required for the pumping of oxygen in the electrochemical pump cell of said nitrogen oxide sensor.

6. The method for controlling engine exhaust gas systems as set forth in claim 1, wherein
the deterioration of at least one of a three-way catalyst and oxygen sensor is detected by comparing a change in control corrected value for the air-fuel ratio of closed loop control referring to an output of said nitrogen oxide sensor with a predetermined value.

7. A method for controlling engine exhaust gas systems, comprising the steps of:
detecting the air-fuel ratio of exhaust gas discharged from an internal engine by an oxygen sensor;
controlling said exhaust gas to near the stoichiometric air-fuel ratio by a closed-loop control using the resultant signal; and
leading said exhaust gas to a three-way catalyst to treat nitrogen oxides, hydrocarbon and carbon monoxide;
wherein a nitrogen oxide sensor is provided downstream of said three-way catalyst; and
the nitrogen oxide concentration is set to a predetermined value by correcting a control value for air-fuel ratio by a closed loop control referring to a signal of said oxygen sensor in accordance with an output of said nitrogen oxide sensor, when in accordance with the extent of correction for the control value of an air-fuel ratio, the deterioration of at least one of said three-way catalyst and said oxygen sensor is detected.

8. The method for controlling engine exhaust systems as set forth in claim 7, wherein
said nitrogen oxide sensor comprises main pump means including an electrochemical pump cell comprising a substrate composed of oxygen ion conductive solid electrolyte, an inside pump electrode and an outside pump electrode formed on the inner surface and outer surface of the substrate, respectively, and the main pump means treating oxygen contained in the measuring gas introduced from an external space by pumping processing on the basis of a control voltage applied between the inside pump electrode and the outside pump electrode, and electric signal conversion means for generating an electric signal corresponding to the quantity of oxygen generated by decomposition or reduction of NOx contained in the measuring gas after treated by the pumping processing by the main pump means in which one side thereof has a pair of detection electrodes formed on the side where the measuring gas that was treated by pumping processing by the main pump means is introduced.

9. The method for controlling an engine exhaust gas system as set forth in claim 8, wherein
the deterioration of at least one of a three-way catalyst and oxygen sensor is detected in accordance with a value of pump current value required for the pumping of oxygen in the electrochemical pump cell of said nitrogen oxide sensor.

10. A method for controlling engine exhaust gas systems, comprising the steps of:
detecting the air-fuel ratio of exhaust gas discharged from an internal engine by an oxygen sensor;
controlling said exhaust gas to near the stoichiometric air-fuel ratio by a closed loop control using the resultant signal; and
leading said exhaust gas to a three-way catalyst to treat nitrogen oxides, hydrocarbon and carbon monoxide;
wherein a nitrogen oxide sensor is provided downstream of said three-way catalyst; and
the nitrogen oxide concentration is set to a predetermined value by correcting a control value for air-fuel ratio by a closed loop control referring to a signal of said oxygen sensor in accordance with an output of said nitrogen oxide sensor, when in accordance with the extent of correction for a change width of the control value of an air-fuel ratio, the deterioration of at least one of said three-way catalyst and said oxygen sensor is detected.

11. The method for controlling engine exhaust systems as set forth in claim 10, wherein
said nitrogen oxide sensor comprises main pump means including an electrochemical pump cell comprising a substrate composed of oxygen ion conductive solid electrolyte, an inside pump electrode and an outside pump electrode formed on the inner surface and outer surface of the substrate, respectively, and the main pump means treating oxygen contained in the measuring gas introduced from an external space by pumping processing on the basis of a control voltage applied between the inside pump electrode and the outside pump electrode, and electric signal conversion means for generating an electric signal corresponding to the quantity of oxygen generated by decomposition or reduction of $NO_x$ contained in the measuring gas after treated by the pumping processing by the main pump means in which one side thereof has a pair of detection electrodes formed on the side where the measuring gas that was treated by pumping processing by the main pump means is introduced.

12. The method for controlling engine exhaust gas systems as set forth in claim 11, wherein
the deterioration of at least one of a three-way catalyst and an oxygen sensor or both is detected in accordance with a value of pump current value required for the pumping of oxygen in the electrochemical pump cell of said nitrogen oxide sensor.

13. The method of controlling an engine exhaust gas system as set forth in claim 11, wherein
the deterioration of at least one of a three-way catalyst and an oxygen sensor is detected in accordance with a change of pump current value required for the pumping of oxygen in the electrochemical pump cell of said nitrogen oxide sensor.

* * * * *